(12) United States Patent
Müller

(10) Patent No.: US 12,357,813 B2
(45) Date of Patent: Jul. 15, 2025

(54) PROCESS FOR TREATMENT OF INTERNAL ORGAN OEDEMA USING AN ELECTRIC CURRENT DELIVERING ELECTRODE SYSTEM AND SYSTEM THEREFOR

(71) Applicant: Berlin Heals GmbH, Berlin (DE)

(72) Inventor: Johannes Müller, Berlin (DE)

(73) Assignee: Berlin Heals GmbH, Berlin (DE)

( * ) Notice: Subject to any disclaimer, the term of this patent is extended or adjusted under 35 U.S.C. 154(b) by 276 days.

(21) Appl. No.: 17/995,100

(22) PCT Filed: Mar. 29, 2021

(86) PCT No.: PCT/EP2021/058201
§ 371 (c)(1),
(2) Date: Sep. 29, 2022

(87) PCT Pub. No.: WO2021/198205
PCT Pub. Date: Oct. 7, 2021

(65) Prior Publication Data
US 2023/0149707 A1    May 18, 2023

Related U.S. Application Data

(60) Provisional application No. 63/001,780, filed on Mar. 30, 2020.

(30) Foreign Application Priority Data

Mar. 30, 2020   (EP) .................................. 20166881

(51) Int. Cl.
*A61N 1/05* (2006.01)
*A61N 1/20* (2006.01)

(52) U.S. Cl.
CPC ............ *A61N 1/05* (2013.01); *A61N 1/0507* (2013.01); *A61N 1/0514* (2013.01);
(Continued)

(58) Field of Classification Search
None
See application file for complete search history.

(56) References Cited

U.S. PATENT DOCUMENTS 5,207,231 A * 5/1993 Fakhri ................. A61N 1/32
607/63
5,817,138 A * 10/1998 Suzuki .................. A61N 1/323
607/67

(Continued)

FOREIGN PATENT DOCUMENTS

EP    3427789 A1    1/2019
WO    9823326 A1    6/1998

(Continued)

OTHER PUBLICATIONS

PCT International Search Report and Written Opinion for PCT/EP2021/058201, mailed Jun. 23, 2021 (14 pages).

*Primary Examiner* — Michael W Kahelin
(74) *Attorney, Agent, or Firm* — Eversheds-Sutherland (US) LLP

(57) ABSTRACT

A process of treatment of internal organ oedema is using an electric current delivering electrode system comprising electrodes to be positioned at two places on the outer surface of the internal organ and/or in a liquid carrying vessel of the internal organ and delivering electric current to induce electro-osmosis between the electrodes. An electrode assembly system for this treatment by electro-osmosis includes, in addition to the two electrodes, a control unit adapted to control the current flow between the two electrodes.

44 Claims, 4 Drawing Sheets

(52) U.S. Cl.
CPC ......... *A61N 1/0587* (2013.01); *A61N 1/0597* (2013.01); *A61N 1/20* (2013.01); *A61N 1/205* (2013.01); *A61N 2001/0585* (2013.01)

(56) References Cited

U.S. PATENT DOCUMENTS

| | | |
|---|---|---|
| 2008/0195163 A1 | 8/2008 | Scharmer |
| 2010/0286746 A1* | 11/2010 | Wariar ................ A61B 5/415 607/42 |

FOREIGN PATENT DOCUMENTS

| | | |
|---|---|---|
| WO | 2017015714 A1 | 2/2017 |
| WO | 2017021255 A2 | 2/2017 |

* cited by examiner

PROCESS FOR TREATMENT OF INTERNAL ORGAN OEDEMA USING AN ELECTRIC CURRENT DELIVERING ELECTRODE SYSTEM AND SYSTEM THEREFOR

CROSS REFERENCE TO RELATED APPLICATIONS

This application claims priority to PCT/EP2021/058201, filed on Mar. 29, 2021, which claims the benefit of European Application No. 20166881.1, filed on Mar. 30, 2020 and U.S. Provisional Application No. 63/001,780, filed on Mar. 30, 2020, the entire contents of which are incorporated by reference herein.

TECHNICAL BACKGROUND

Technical Field

The present invention relates to a process of treatment of internal organ oedema using an electrical current delivering electrode system comprising two electrodes to be positioned at two places on or close to the internal organ or in liquid carrying vessels as part of the organ or in the internal organ as well as a device for the reduction up to removal outside of internal organ oedema and a system, therefor.

TECHNICAL CONSIDERATIONS

Primary or secondary disease of an organ, acute or chronic infections or a reduced blood supply to organs are often associated with oedema of the affected organ, which can severely impair the function of the organ. In the heart, this is particularly evident in the form of a restriction of the pumping function, which has an effect on all organs of the body. Thus, internal organ oedema relate to myocardial oedema as described in the following prior art articles but also to kidney oedema or liver oedema to name specific internal organs. Reduced pumping function of the heart typically leads to a congestion of blood in other dependent organs (e.g. liver, kidney), which impresses as oedema in these organs. The extent of the oedema in these organs depends on the severity of the heart dysfunction. Organ oedema can also occur independently of a reduced pumping function of the heart in organ-specific diseases (e.g. diseases of the kidney or liver), such as nephrotic syndrome or inflammation of the liver.

The article "Myocardial Edema on T2-Weighted MRI—New Marker of Ischemia Reperfusion Injury and Adverse Myocardial Remodeling" by Yuko Tada and Phillip C. Yang in http://circres.ahajournals.org DOI: 10.1161/CIRCRESAHA.117.311494; identifies myocardial oedema as problematic within myocardial infarction patients and suggests new marker therefor. No specific treatment is mentioned.

The article "Why Edema Is a Matter of the Heart" by Matthias G. Friedrich, in http://circimaging.ahajournals.org DOI: 10.1161/CIRCIMAGING.117.006062 explains the important relationship between myocardial oedema and myocardial infarction and the possibility to differentiate between acute and remote myocardial infarction based on oedema-sensitive CMR (for cardiac magnetic resonance).

In the European Journal of Heart Failure, vol. 2018, edited by the European Society of Cardiology, Thomas M. Gorter answered in a letter to the editor "Myocardial oedema and congestive heart failure: one piece of the puzzle? Reply" on pp827-828, myocardial oedema is mentioned to be an interesting topic for research in view of the link with heart failure.

In "Global myocardial oedema in advanced decompensated heart failure" by Frederik H. Verbrugge et al. in European Heart Journal—Cardiovascular Imaging (2017) 18, pp787-794 doi:10.1093/ehjci/jew131 it is disclosed that cardiac magnetic resonance (CMR) imaging with quantitative T2 mapping can be used to identify myocardial water content in patients and evaluate the change with decongestive therapy.

Ranjeet M. Dongaonkar et al. shows in "Myocardial microvascular permeability, interstitial oedema, and compromised cardiac function" in Cardiovascular Research (2010) 87, pp331-339 doi:10.1093/cvr/cvq145 the relevance of myocardial oedema as common pathology within instability of the heart. It stipulates that the resolution of myocardial oedema does not restore normal cardiac function. The resolution of myocardial oedema with cardioplegia by avoiding systemic haemodilution is reported.

Maekawa H, Toda G. *Nihon Rinsho.* (2005; 63(1):80-84) have described the negative impact of the storage of water (edema) in the liver for liver function.

In the same way Siddall EC and Radhakrishnan J. (The pathophysiology of edema formation in the nephrotic syndrome. *Kidney Int.* 2012; 82(6):635-642. doi:10.1038/ki.2012.180) describe the importance of an oedema in the kidney, as it occurs in the nephrotic syndrome.

SUMMARY OF THE INVENTION

Based on the above mentioned prior art documents, it can be seen that several methods are applied to correctly identify myocardial oedema but beside the use of cardioplegia by avoiding systemic haemodilution, no treatments are disclosed in the prior art. Therefore, it is an object of the present invention to provide a process which is capable to reduce internal organ oedema and especially myocardial oedema with quite simple means. Astonishingly, it has been found that application of electrical current as such, especially DC current, between two electrodes provided on an internal organ or in liquid carrying vessels in the internal organ over hours immediately starts to reduce the swelling (oedema) and further beneficial results appear if the current application is maintained up to days, weeks or even long-term (chronically).

A liquid carrying vessel can be a blood vessel or a vessel of the lymphatic system or one of the two main cavities (right or left ventricular cavity) of the heart.

When the process is used to reduce myocardial oedema, then the electrodes are positioned on or near by or in the heart at positions taken from the group comprising inside the right ventricle, inside the coronary sinus, on the outside of the left ventricle and/or on the outside of the right ventricle. Regardless of where the electrodes are placed (for example even subcutaneously or outside the human body), it is only relevant that the current flows through the affected organ.

When two outside mounted electrodes are used, these can be flat electrodes (so called patch electrodes); when an outside mounted electrode is connected with an inside mounted electrode these can be realized as a flat electrode and a coil electrode, respectively. If two inside mounted electrodes are used, they usually are coil electrodes. Then the volume of the treated organ, i.e. the region where the current passes, is usually smaller than if at least one flat electrode is used. The electrode according to the invention for reducing oedema of internal organs through application of an electrical current, e.g. a direct current, comprises an electrode support and at least one electrically conductive electrode surface which is embedded in the electrode support, wherein the electrode surface is connected to a control and power supply unit by way of electric lines.

The predetermined current density on the electrode can be maintained by controlling/regulating the current or the voltage. The current density can be maintained, in particular, for a time period starting from several minutes up to days, i.e. longer than 24 hours. Subsequently, it is possible but not necessary to provide a direct current having the opposite polarity.

In both cases the direct current application provides electro-osmosis or an osmotic like effect which generates the secretion of water droplets usually at the cathode, however, depending on the composition of the liquid (electrical charge carriers in the liquid) to be removed, the liquid can also be secreted at the anode. The electroosmosis or electroosmosis-like effect can also affect the lymphatic system in the sense that increased lymph is drained from the organ tissues (interstitium) via the lymphatic system, thus reducing oedema.

In the case of patch electrodes, it is possible to provide a one-way valve within the patch surface, preferably surrounded by the electrode surface. As a result, the fluid is drained at the point where it has the greatest negative influence on the contact between the electrode surface and the surface of the organic tissue.

Preferably, such a one-way valve is a diaphragm valve having a valve diaphragm.

The process of reduction of the internal oedema applies steps for controlling the current density (J) on the electrode according to the present invention wherein the current (I) flowing through the electrode is regulated in such a way that a current density (J) provided within a predetermined interval for the electrode surface is maintained. Alternatively, the current density (J) is maintained around a predetermined value for the electrode surface.

Due to the selection of a current density interval, no adjustments of the presetting of the current density are necessary in this interval.

If the current density is regulated around a predetermined value, a treatment-specific current density can be set, which is particularly advantageous since providing a predetermined electroosmotic effect.

In case of segmented electrodes, e.g. that different parts of a coil electrode are electrically separated one from another or that a flat electrode is separated into to electrically separated electrode surfaces, a control unit can achieve that the current density on each electrode part is maintained in such a predetermined interval.

Each electrode according to the invention can be used as a current-feeding or current-receiving electrode, wherein the cathode is the electrode where the maximum water is gathered and conducted away. Therefore, an important reduction effect of the internal oedema happens where the anode provides the water-reduced area.

The process of treatment of internal organ oedema can comprise different current delivering electrode systems. The always comprise two electrodes and a control unit. The two electrodes are to be positioned at two places in relation to the internal organ to be treated and the electrodes are connected to the control unit. The control unit is then adapted to deliver an electric current to induce electro-osmosis.

In one embodiment there are provided two patch electrodes, which can be one-surface electrodes or comprises a plurality of separated segments. Then the patch electrodes are mounted on the outer surface of the internal organ, which can be heart, kidney or liver. Mounted can comprise positioning or attaching. It is also possible to position the patch electrodes just subcutaneously or on the outside of the skin of the patient.

According to one embodiment of the present invention, the electrodes are positioned extracorporally, preferably in physical contact to the skin of a patient. Within the present invention, a place on the outer surface of an internal organ may also include a place on the external skin surface and/or the outer surface of an internal organ may include the external skin surface.

In addition to the aforementioned conditions, myocardial oedema plays a crucial role in the further course of the disease in patients with fresh myocardial infarction or acute myocarditis. A myocardial infarction or myocarditis that cannot be controlled because of myocardial oedema has an increased likelihood of fatal consequences.

Since under acute conditions it is not possible to apply the electrodes directly to an affected internal organ, as this would require a surgical intervention, albeit a minor one, electrodes are envisaged herein that apply the current with its inherent field or the electric field transdermally (with physical contact to the skin).

It is clear to the skilled person that electrodes which are to be positioned extracorporally are structurally different to electrodes to be positioned on internal (intracorporal) organs. Thus, according to one preferred embodiment of the present invention, the electrodes of the present invention and/or the electrode assembly system of the present invention are adapted to allow an extracorporal application thereof. Generally, the size of the electrodes of the present invention may be selected depending on the size of the person to be treated. In a preferred embodiment, the electrodes to be applied extracorporally are patch electrodes.

For any use according to the invention, and in particular for an external or extracorporal use or application of the electrodes according to the present invention, patch electrodes having a size in the range of from 2 by 2 cm (for babies or infants) up to 30 by 40 cm (for adults), and/or a surface area of from 4 cm$^2$ to 1200 cm$^2$, or any size or surface area in between may be employed. Also, electrodes of different shapes or forms may be used, comprising round, elliptical, square, rectangular and freeform.

In one embodiment of the present invention, the electrodes contacting the skin are electrically conductive allowing electrical current to flow. In one embodiment of the present invention, at least one or all electrodes contacting the skin is/are electrically insulated allowing an electrical field to be generated without any current flow.

To ensure a good transition between the skin and the electrode with as little energy loss as possible, a gel or other liquid with high conductivity may be applied between the extracorporally applied electrode and the skin, similar to substances used for external defibrillation.

Since anti-edematous therapy may require a longer duration of application of the electrodes, one embodiment of the present invention features adhesive electrodes which may be reversibly and directly fixed to the skin surface, preferably wherein the adhesive itself has a favorable resistance behavior. Preferably, the electrically conductive surface of the extracorporal electrode(s) is designed to be deformable so that the electrode(s) can adapt to the body contours.

Generally, the electrically conductive electrode surface may be connected via an electrical energy conducting cable to a device that can generate and deliver the corresponding currents and voltages.

In another embodiment a patch electrode is combined with a coil electrode, wherein the patch electrode is positioned on the outer surface of the internal organ, wherein the coil electrode is positioned in a liquid carrying vessel of the internal organ. Then the current is flowing through the organ between the electrode in the blood or lymphatic duct vessel and the outside of the organ.

When the internal organ is the heart, the patch electrode is positioned for the heart on the epicardial side of the heart and wherein the coil electrode is positioned for the heart inside the ventricular cavity.

When the internal organ is the kidney, the patch electrode is positioned for the kidney on the outer side opposite to the renal artery and renal vein and wherein the coil electrode is positioned inside the renal artery and renal vein or the renal pelvis.

Finally, a process of treatment of internal organ oedema can also use two coil electrodes, wherein the two coil electrodes are positioned in different liquid carrying vessels within the same internal organ. Then the current flow is restricted between the core parts of the organ where the coil electrodes are positioned.

Within this embodiment in an application for the heart, one of the two coil electrodes can be placed in the coronary sinus and the other of the two electrodes can be positioned in the right or left ventricular cavity.

As mentioned above, the internal organ oedema to be treated can be a myocardial oedema or an oedema of the kidney or an oedema of the liver.

The electro-osmosis is generated for a reduction up to a removal of the internal organ oedema.

The electroosmotic effect comprises an accumulation of oedema fluid at the electrodes to be carried away from the electrodes. Additionally, said electroosmotic effect is to drain an accumulation of oedema fluid from the tissue (interstitium) of an organ by stimulating the lymphatic system of the corresponding organ to more rapidly remove the accumulated oedema fluid.

The current delivered to the electrodes and flowing through the organ can be preferably a direct current. The direct current can be an amplitude modulated direct current, i.e. a direct current wherein the intensity of current is modulated around an average value.

The control unit can be configured to switch the polarity of the direct current in predetermined time intervals. Such predetermined time intervals can comprise intervals between 1 hour and 7 days. The entire process can comprise a treatment time of several days up to several months.

It is noted that an electric current flowing between two electrodes is accompanied by electrolysis generating a pH shift in the area of the interface between electrode conducting surface and tissue and creation of gas. Since the current density is small and the electrodes are preferably made of platinum or a platinum iridium alloy (or another metal from the electrochemical series with high positive electrical voltage), the effects are limited. It is even so that the shift of the pH towards alkaline can have a beneficial effect on the tissue as inflamed tissue often has a pathological (acid) pH value. The gas generation is effected at the anode which is preferably in the flowing blood (in the blood vessel). The liquid is capable to dissolve the gas. The generated gas is especially $Cl_2$ which—immediately after its formation, forms bonds that are physiological and therefore harmless. The existence of an electrolysis effect, even if small, is a difference between any application of AC currents to internal organs.

The invention further comprises an electrode assembly comprising two electrodes and a control circuit, wherein the first and second electrodes are electrically connected to the control circuit, wherein the control unit is adapted to establish a direct current flow between the first and the second electrode.

The electrode assembly has preferably a control unit being adapted to switch the polarity of the current flow between the first and second electrodes.

The electrode assembly can comprise two patch electrodes to be positioned opposite one the other of the internal organ so that the current flow between the first and second electrodes is traversing the internal organ.

The electrode assembly can have a mixed lay-out with one coil electrode and a patch electrode, wherein the coil electrode is to be positioned inside a liquid vessel of the internal organ and the patch electrode is to be positioned outside of the internal organ so that the current flow between the first and second electrodes is traversing the internal organ oedema part.

The electrode assembly can have two coil electrodes to be positioned both inside in different liquid vessels of the internal organ so that the electric current flow between the first and second electrode is traversing through the internal organ oedema part especially between the two liquid vessels.

The control unit of the electrode assembly can be adapted to control the strength of the current flowing between the first and second electrodes to control the strength of the electric current flow through the place of the internal organ oedema over time.

BRIEF DESCRIPTION OF THE DRAWINGS

Preferred embodiments of the invention are described in the following with reference to the drawings, which are for the purpose of illustrating the present preferred embodiments of a device to execute the process according to the invention and not for the purpose of limiting the same. In the drawings.

DESCRIPTION OF PREFERRED EMBODIMENTS

Figure 1:
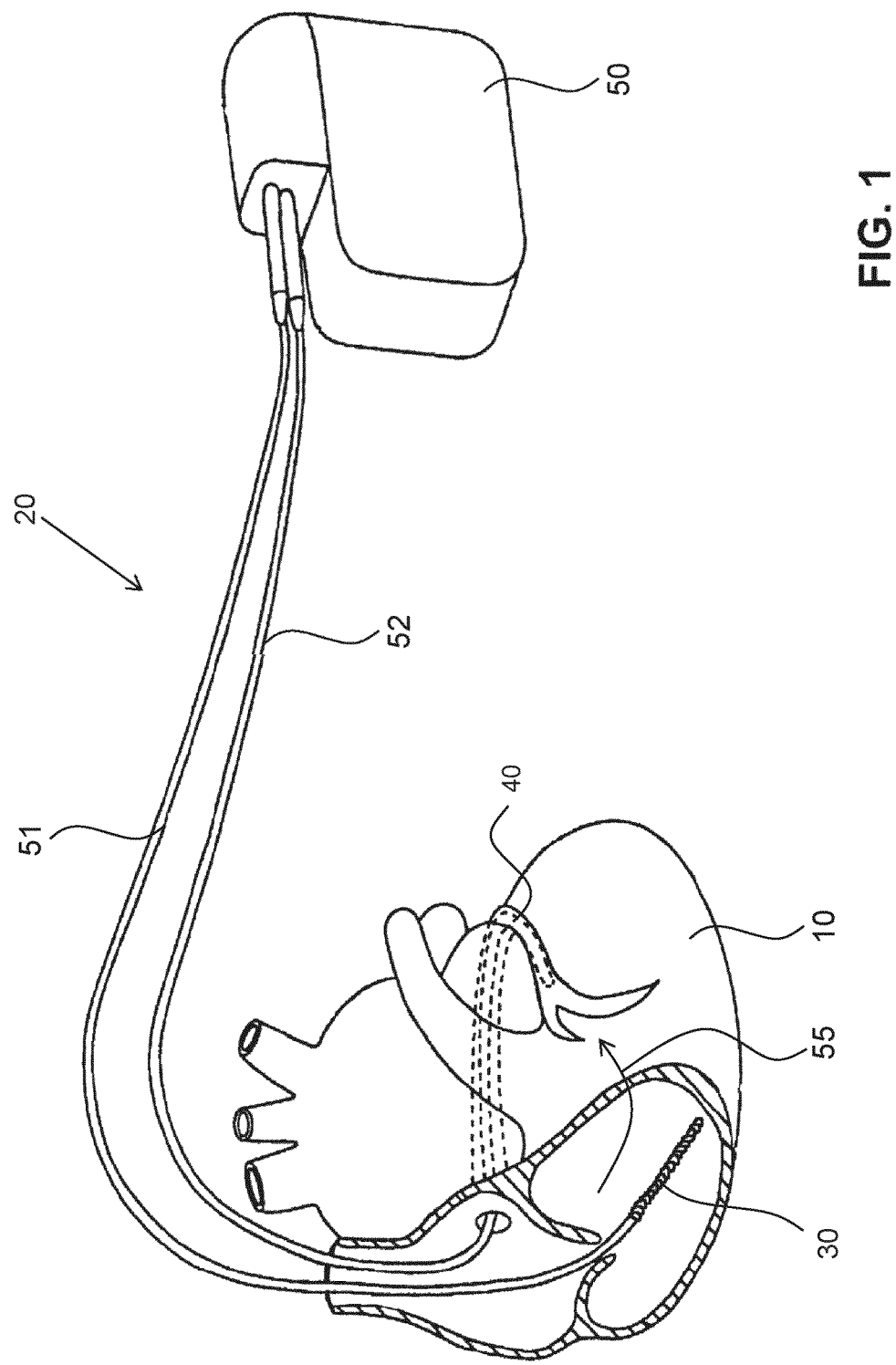
FIG. 1 shows a two internal electrode disposition (two internal coil electrodes) of electrodes in the heart as internal organ.

FIG. 1 shows a schematic representation of a heart 10 with an electrode assembly 20 according to a first illustrative embodiment of the invention. The implantable direct-current electrode assembly 20 comprises two implantable electrodes 30 and 40 and a control circuit 50, usually arranged in a separate housing in which the battery for the power supply is likewise provided.

The two electrodes 30 and 40 are connected to the control circuit 50 via two single-conductor cables 51 and 52.

The control circuit 50 is designed to establish a potential difference between the two electrodes 30 and 40, such that a direct current can flow between these electrodes 30 and 40.

One electrode 30 is a ventricular electrode, provided for positioning in the right ventricle, and is designed as a coil electrode. It is therefore designated below as a ventricular coil electrode 30. The length of the ventricular coil electrode 30, defined by the one conductive metallic sheath surface or coil surface defining a sheath, is ca. 4 to 10 centimeters and is designed to fill as far as possible the entire length of the right ventricle after passage through the right cardiac tricuspid valve. Here, the ventricular coil electrode 30 is placed loosely into the right ventricle, but it can touch the wall of the right ventricle. To prevent the electrode from falling into the outflow tract of the right ventricle (pulmonary valve), it is anchored actively (by screw) with its tip or passively with barbs in the tip of the right ventricle which hook into the trabecular meshwork of the right ventricle and thus fix the electrode tip.

Figure 2:
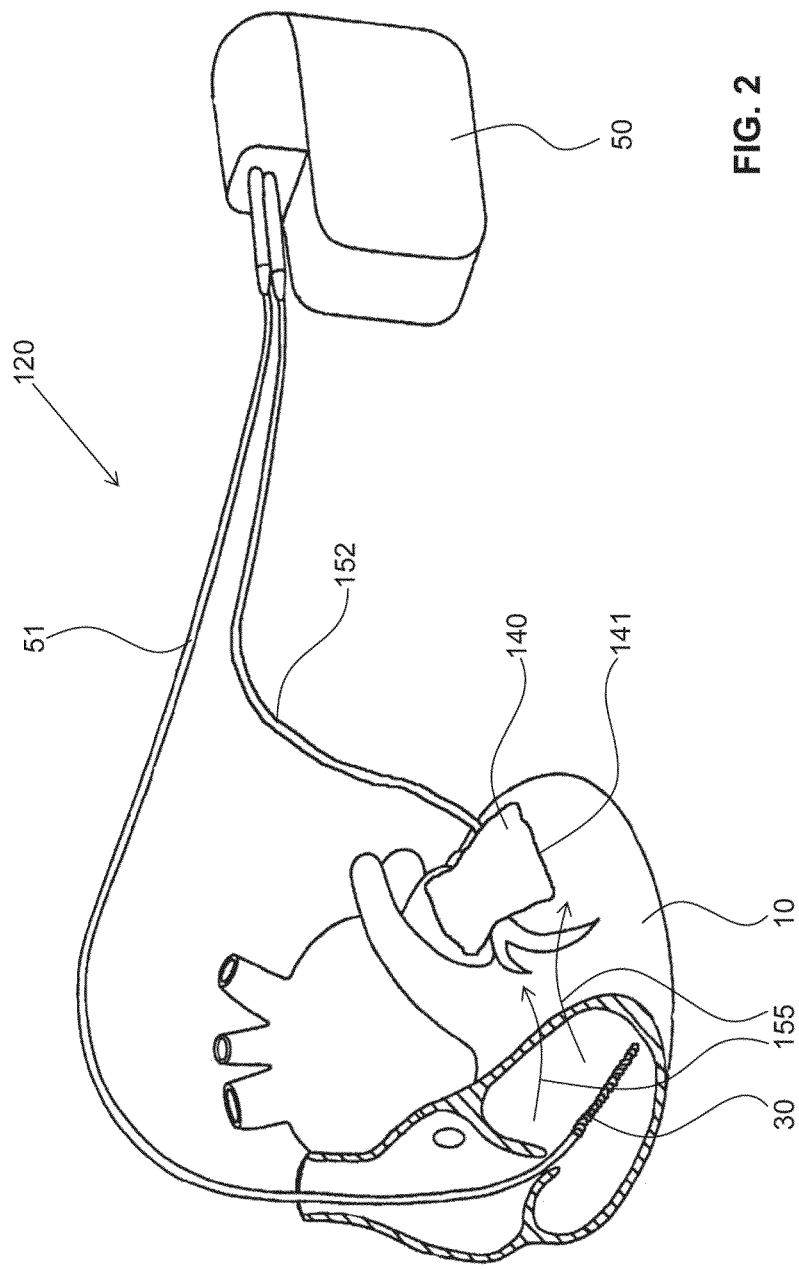
FIG. 2 shows a mixed (one internal coil electrode, one external patch electrode) disposition of electrodes in and outside the heart.

From FIGS. 1 and 2, the electrode 30 seems to float freely in the right ventricle. However, this is only apparently the case, because the figures are schematic two-dimensional depictions. Generally, the electrode 30 will nestle on the wall of the ventricle; in the depiction in FIG. 2, this could be the posterior wall, which is not visible there. The electrode 30 is flexible in order to adopt these gentle curvatures, which amount to less than 30 degrees with respect to the longitudinal axis.

The other electrode 40 of FIG. 1 is a coronary sinus electrode, provided for positioning in the coronary sinus, and is likewise designed as a coil electrode. This coronary sinus coil electrode 40 has a smaller diameter than the ventricular coil electrode 30 since it is intended to be advanced far into the coronary sinus in order then to come to lie in the narrowing end region there. This electrode thus lies at a position substantially predefined by the vessel walls, which position the operating surgeon otherwise establishes by advancing it in the longitudinal direction.

When the two electrodes 30 and 40 are subjected to a potential difference by the control circuit 50 via the attachment wires or cables 51, 52 insulated from the environment, a direct current then flows according to the arrow 55 through the myocardium. In a manner predetermined by the control circuit, the electrode 30 can be the cathode for a predetermined time of between a few minutes and up to chronically, whereby the direction of the current is predefined. The control circuit can then change the direction of the current after a correspondingly predetermined time, whereby the electrode 40 becomes the cathode. The current strength can also change, since the resistance between the two electrodes 30 and 40 is dependent on the direction of the current. In a further illustrative embodiment, the control device controls the current strength at a uniform predetermined value. The DC current can have a constant value or can be amplitude modulated with a modulation height of e.g. +−10% to +−25% of the average DC value.

FIG. 2 shows a schematic representation of a heart 10 with an electrode assembly 120 according to a second illustrative embodiment of the invention. The implantable direct-current electrode assembly 120 comprises two implantable electrodes 30 and 140 and also a control circuit 50.

Identical features are provided with identical reference signs, similar features with correspondingly similar reference signs.

The control circuit 50 can be designed in the same way as described in FIG. 1. The two electrodes 30 and 140 are also connected to the control circuit 50 via two single-conductor cables 51 and 52.

The control circuit 50 is also designed here to establish a potential difference between the two electrodes 30 and 140, such that a direct current can flow between these electrodes 30 and 140 for a predetermined time of several minutes, e.g. 5 minutes, to several days, e.g. 3 days or even chronically.

One electrode 30 is once again a ventricular electrode, provided for positioning in the right ventricle, and is designed as a coil electrode. It is therefore also designated here as a ventricular coil electrode 30. The length of the ventricular coil electrode 30, defined by the one conductive metallic sheath surface or coil surface defining a sheath, is ca. 4 to 10 centimeters and is designed to fill as far as possible the entire length of the right ventricle in the longitudinal axis after passage through the right cardiac valve (tricuspid valve). Here, the ventricular coil electrode 30 is placed loosely into the right ventricle, is passively anchored at the distal end and can bear on the wall of the ventricle or on the septum. To prevent the electrode from falling into the outflow tract of the right ventricle (pulmonary valve), it is anchored actively (by screw) with its tip or passively with barbs in the tip of the right ventricle.

The other electrode 140 is a surface electrode (patch electrode), provided for positioning on the epicardium, the pericardium or close to the epicardium (e. g. even subcutaneously). It can be designed, for example, according to the teaching of US 2008/0195163 A1. This surface electrode 140 is applied to the left side of the myocardium, epicardially opposite the right ventricle.

When the two electrodes 30 and 140 are subjected to a potential difference by the control circuit 50 via the attachment wires or cables 51, 52 insulated from the environment, a direct current then flows according to the arrows 155 through the myocardium. This flow of current is symbolized here by two arrows which essentially show the approximate current flow direction, since the flow of current here fans out from a substantially longitudinally dimensional face of the substantially longitudinally oriented surface of the coil electrode 30 toward the surface electrode 140 and thus sweeps across a fan. Seen physically, the direct current flows through a prism; that is to say proceeding from an edge (of the prism) to its base on the patch electrode.

A prism is by definition a geometric body whose side edges are parallel and of equal length and which has a polygon as base. It arises from parallel displacement of a plane polygon along a straight line not lying in this plane and is therefore a special polyhedron. Here, the straight line is predefined by the longitudinal axis of the coil electrode 30, and the polygon is a triangle with the apex at the coil electrode 30 and with a base that corresponds to the width of the surface electrode (patch electrode) 140. If these side edges 141 of the surface electrode 140 do not come to lie parallel to the orientation of the coil electrode, it is a rotated prism. In all cases, the two electrodes 30 and 140 define a not inconsiderable spatial body which guarantees that the direct current emitted by the control circuit 50 flows through a likewise not inconsiderable sub region of the left cardiac muscle and to a slightly lesser extent also of the right cardiac muscle. Describing the geometry of the body through which the current flows as a prism is an approximation, since it can be assumed from this that the electrode does not float freely but is instead passively fixed at its distal tip and then bears on the wall of the ventricle. The boundary lines of the body are then certainly not straight but curved, and the defined body is then obtained only approximately as a prism. Of importance, however, is the narrow "edge" on the one side formed by the coil electrode, and the "broad bottom face" on the other side which is formed by the patch electrode.

Figure 3:
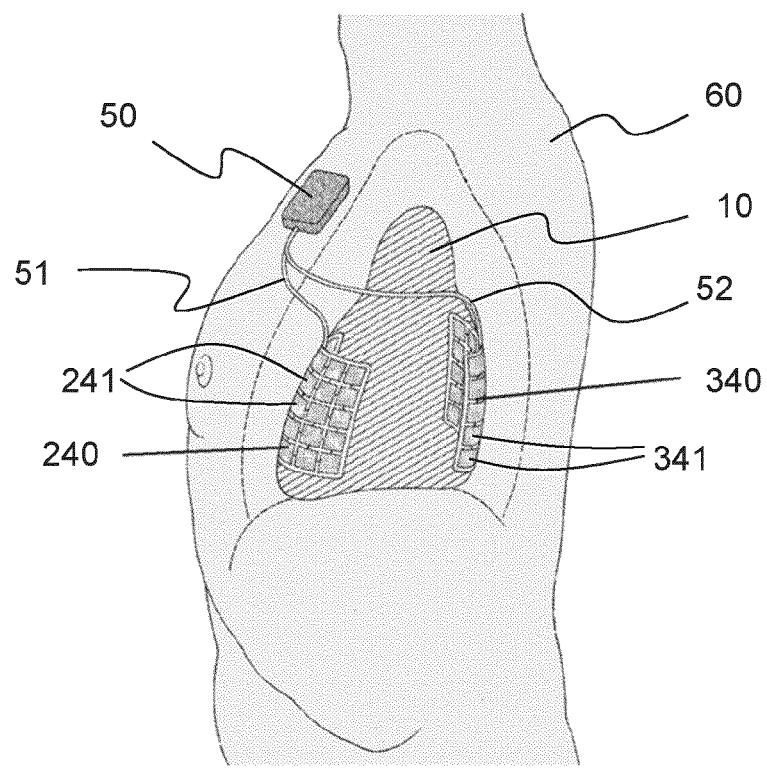
FIG. 3 shows a two external electrodes (external patches with segmented electrodes) disposition of electrodes on external heart surfaces according to the invention during use.

FIG. 3 shows two patch electrodes 240 and 340 which are connected with lines 51 and 52 to a control and power supply unit 50. Here, each patch electrode 240 and 340 as such is a segmented electrode 240 or 340. This means, each electrode 240 or 340 is or comprises a plurality of electrode segments 241 or 341 which are shown as smaller rectangles in FIG. 3. Given, for example, an electrode surface of a patch electrode 240 or 340 which is 100 square centimeters in size in total, and a direct current I of 1 milliampere, the current density is 0.01 milliamperes per square centimeter. If the electrode surface (here a plurality of the electrode segments 241 or 341 detaches from the tissue, e.g. then only 10 square centimeters (i.e., one-tenth), for example, are still in contact, in which current can flow. If constant-current regulation were applied, the current density would increase ten-fold, to 0.1 milliamperes per square centimeter, since the area has become ten times smaller due to the detachment. Such high current densities are undesired, since they can trigger cardiac arrhythmia, for example, and are therefore preferably controlled in control unit 50. Therefore, usually, current densities between 0.1 to 100 microampere per square centimeter are applied, preferable 1 to 10 microampere per square centimeter.

Although the organ 10 can be a heart, it is also possible that the organ 10 is a kidney with applied electrodes 240 and 340. In other embodiments it could be a liver.

Figure 4:
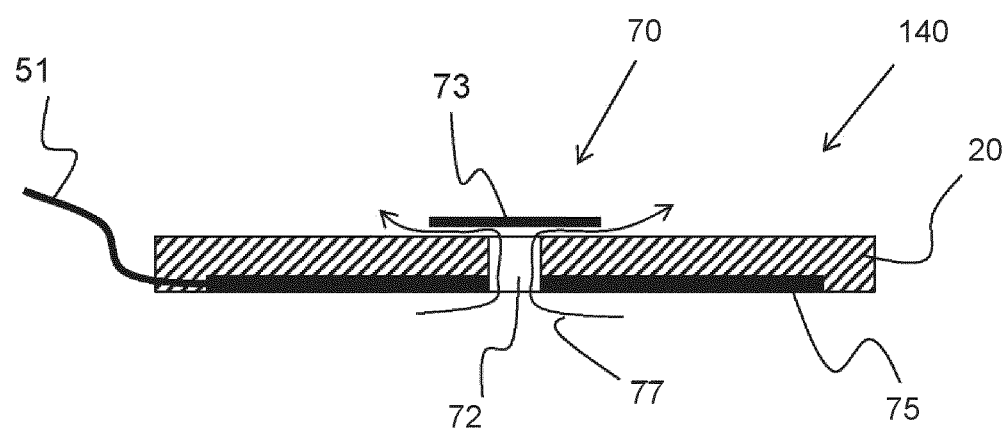
FIG. 4 shows an electrode according to the invention comprising a one-way valve.

The electrode 1 optionally comprises at least one one-way valve 70 which essentially comprises an opening 72 and a diaphragm 73 covering the opening 72 on the far side of the internal organ. A schematic sectional view of the one-way valve 70 is depicted in FIG. 4. The diaphragm is made from silicone, for example. The one-way valve 70 is situated within the electrode surface 75.

The apparatus as described in connection with FIG. 1, 2 or 3 delivers an electric current, e.g. a direct current, to the internal organ, here the heart. This electric current, e.g. a direct current, acts immediately or at least extremely fast on the internal organ, here the heart.

Extremely fast means that the first signs of improvement starts to appear within minutes after the current begins to flow. Irrespective of the fact that the patient describes a better feeling of well-being, echocardiography can be used to objectify a reduction in the size of the ventricle very quickly as the first positive sign. In this short period of time, this immediate improvement cannot be explained by molecular biological processes in the heart musculature; the improvement is due to electro-osmosis, a process by which water is transported osmotically (used, for example, to dry damp walls or in cosmetics).

It can be assumed that diseased organs are always also inflamed organs and inflammation is always associated with oedema. In relation to the heart, this means that there is an intra- and/or extracellular excess of fluid (oedema), which causes the heart muscles to swell and limits their pumping function. By applying an electric field or voltage, an osmotic like effect is induced, by which water is extracted from the heart muscles, which was before enlarged and bloated by oedema. This effect is transferable to other internal organs in which the intra- and/or extracellular excess of fluid (Oedema) leads to restricted cell function and thus reduces organ function as a whole.

This function is based on the insight, that the human body is a so-called ion conductor. The electric current mainly causes ion movement (electrokinesis), i.e. the migration of negatively charged anions (e.g. $Cl-$, $CO_2-$ etc.) to the anode and of positively charged cations (e.g. $Na+$, $Mg++$.etc.) to the cathode. Electro-chemical reactions occur on metals (electrodes, but also metallic foreign bodies). A migration of protein fractions (electrophoresis) and a shift of water in the direction of the cathode (electro-osmosis) takes place in the applied direct current field. In addition, the electroosmosis or electroosmosis-like effect induced by the applied current field supports and enhances drainage through the lymphatic system. The effect is as such independent from the application with two internal coil electrodes, one coil electrode and one patch electrode or two patch electrodes applied on opposite parts of the internal organ like the on the left and the right ventricle.

Especially in the case of direct currents, there is the theoretical risk of undesirable burns. Within the application of currents with densities in the range of 0.01 to 0.1 milliamperes per square centimeter (which is in the range that can be find in the human body physiologically), the effect of electro-osmosis can be maintained chronically without changing the polarity to enhance the water draining effect on the treated organ. Within the context of the present invention, "water" is mentioned solely as an example for the aqueous solution(s) present within the body and may be replaced by the term "aqueous solution" wherever appropriate.

This can be achieved with electrodes in the blood vessel system or outside of the organ in question.

Although the drawings only show the heart in the application, similar coil electrodes can be used for the treatment of a liver and/or a kidney. This can be used in blood vessels or the lymphatic system. Flat electrodes can be positioned on or near the liver or kidney with the flat electrodes on mainly opposite sides of the organ, so that the current passes through the organ. This can also be done subcutaneously or from the exterior of the human body.

As an example of the clinical success of the above described effects achieved by directly controlling an electric field applied onto the oedema-afflicted organs or vessels, the following results have been reported (Kosevic, D et al. (2021). Cardio-microcurrent device for chronic heart failure: first-in-human clinical study. ESC heart failure. 10.1002/ehf2.13242).

The average of patients included in the study reported therein is a New York Heart Association (NYHA) Class III non-ischemic patient in the age group of 29 to 67 years, with a body mass index of 22.5 to 35.9 and a history of heart failure, and in particular with a significantly reduced left ventricular ejection fraction (LVEF) and a 6 minute walk under about 250 m. The "6 min walk test" or "6MWT" has been developed by the American Thoracic Society as a reliable indicator in the form of a sub-maximal exercise test for assessing aerobic capacity and endurance, wherein the walking distance covered over a time of 6 minutes by the patient is used as the outcome by which to compare changes in performance capacity. Here, the average patient (as described before) achieved between ~170 and ~250 m at hospitalization, between ~350 and ~450 m after 14 days, and between ~370 and ~470 m after 6 months of device use, and, furthermore, the average patient's classification according to the NYHA improved to a significantly less critical class after this time period.

Figure 5:
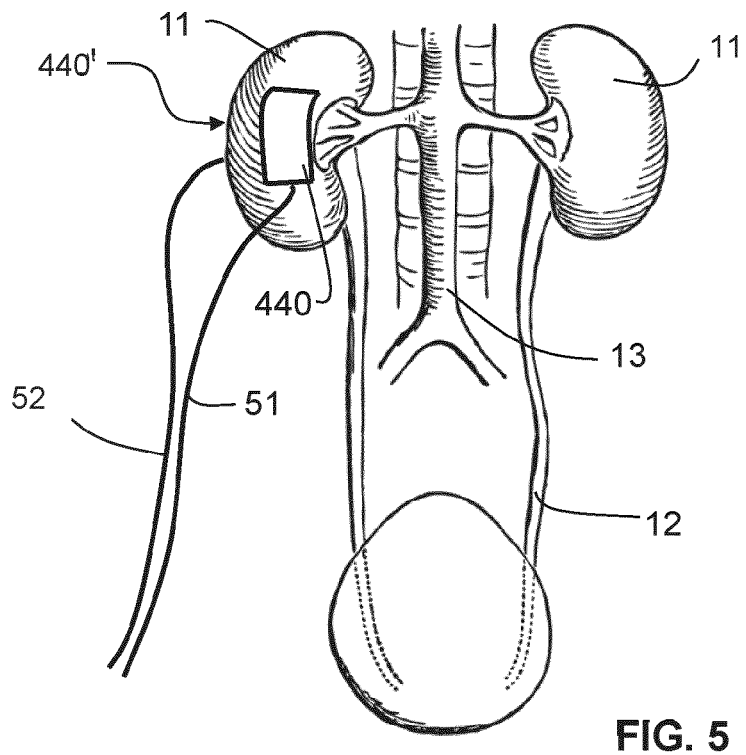
FIG. 5 shows a two external electrodes (external patches with single electrodes) disposition of electrodes on external kidney surfaces according to the invention during use.

FIG. 5 shows a two external electrodes (external patches with single electrodes) disposition of electrodes on external kidney surfaces according to the invention during use. There are two kidneys 11 with a symbolic central aorta or vena renalis 13. Ureters 12 connect the kidneys 11 with the bladder of the person. A patch electrode 440 is positioned on the outside of one kidney 11. A second patch electrode 440' (with an identical outlay to the first patch electrode 440) is positioned on the opposite side of the kidney 11. Therefore, the core part of the kidney with its renal pyramids 17, renal calix 16 and the renal pelvis 18 is positioned between the two patches 440 and patches 440'.

The flat electrode patches 440 and 440' are connected with a control unit 50, not shown in FIG. 5, via connection lines 51 and 52, respectively. The supply lines 51 and 52 provide a current flow between the flat electrode patches 440 and 440' which current then effectively flows through the mentioned parts of the kidney to reduce the oedema through electro osmotic effects. The electrode patches 440 and 440' are shown as single electrodes but can also be segmented electrodes as shown in FIG. 3.

Figure 6:
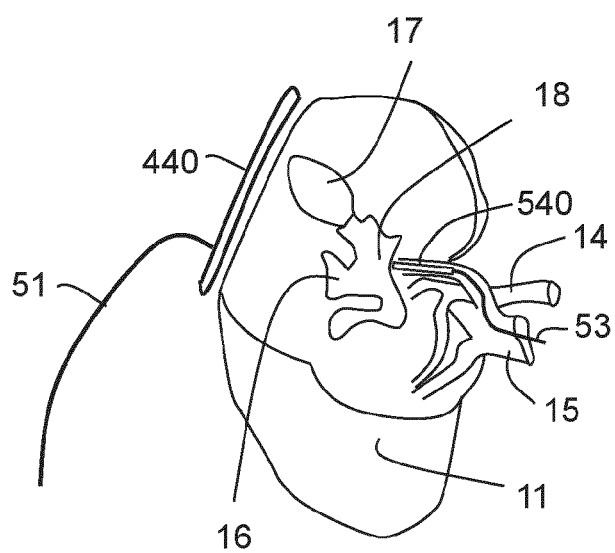
FIG. 6 shows a mixed (one internal coil electrode, one external patch electrode) disposition of electrodes in and outside the kidney.

FIG. 6 shows a mixed (one internal coil electrode, one external patch electrode) disposition of electrodes in and outside the kidney. The kidney 11 is shown with its renal pyramids 17, renal calix 16 and the renal pelvis 18. The aorta renalis 14 and vena renalis 15 are shown as well. A first external electrode 440 is connected via line 51 to a control unit 50 (not shown). A renal coil electrode 540 is positioned in the vena renalis 15 to allow a current flow between this electrode 540 and said external patch electrode 440. The connection of the renal coil electrode 540 to the control unit 50 is effected via the catheter line 53 used to position the renal coil electrode 540. The coil electrode could in other embodiments also positioned in the renal lymphatic system.

LIST OF REFERENCE SIGNS

| | |
|---|---|
| 10 | heart (internal organ) |
| 11 | kidney (internal organ) |
| 12 | ureter |
| 13 | aorta or vena renalis |
| 14 | aorta renalis |
| 15 | vena renalis |
| 16 | renal calix |
| 17 | renal pyramid |
| 18 | renal pelvis |
| 20 | electrode assembly |
| 30 | ventricular coil electrode |
| 40 | coil electrode for coronary sinus |
| 50 | control circuit |
| 51 | single-conductor supply line |
| 52 | single-conductor supply line |
| 53 | renal catheter line |
| 55 | arrow indicating DC current flow |
| 60 | person |
| 70 | patch electrode surface |
| 72 | opening |
| 73 | diaphragm valve |
| 75 | electrode surface |
| 77 | water flow |
| 140 | external patch electrode |
| 141 | edge of the surface electrode |
| 152 | single-conductor supply line |
| 155 | arrow indicating DC current flow |
| 240 | first external patch electrode |
| 340 | second external patch electrode |
| 440 | first external patch electrode |
| 440' | second external patch electrode |
| 540 | renal coil electrode |

The invention claimed is:

1. A method for treating internal organ oedema, comprising positioning a first electrode and a second electrode on or inside a subject such that that an electric current flow between the first and second electrodes traverses through the internal organ oedema of the subject; and delivering a controlled electric current between the electrodes to the internal organ oedema, wherein the electrodes are connected to a control unit adapted to deliver the electric current to a preset value to induce electro-osmosis, wherein the preset value is maintained by controlling a voltage between the first electrode and the second electrode for any given distance between the electrodes, wherein the first electrode is a patch electrode and the second electrode is a coil electrode.

2. The method of claim 1, wherein the current is a direct current.

3. The method of claim 2, wherein the direct current is an amplitude modulated direct current.

4. The method of claim 2, wherein the control unit is configured to switch the polarity of the direct current in predetermined time intervals.

5. The method of claim 4, wherein the predetermined time intervals comprise intervals between 10 minutes and three months.

6. The method of claim 5, wherein the predetermined time intervals comprise intervals between 24 hours and 7 days.

7. The method of claim 1, wherein the control unit is configured to cause and maintain the strength of the electric current at the preset value independently of external influences.

8. A method for treating internal organ oedema, comprising positioning a first electrode and a second electrode on or inside a subject such that that an electric current flow between the first and second electrodes traverses through the internal organ oedema of the subject; and delivering a controlled electric current between the electrodes to the internal organ oedema, wherein the electrodes are connected to a control unit adapted to deliver the electric current to a preset value to induce electro-osmosis, wherein the preset value is maintained by controlling a voltage between the first electrode and the second electrode for any given distance between the electrodes, wherein the first electrode is positioned in the coronary sinus of the heart and the second electrode is positioned in the right or left ventricular cavity of the heart.

9. The method of claim 8, wherein the control unit is adapted to charge the first electrode negatively and the second electrode positively, and the control unit is adapted to directly control a strength of the electric field induced by the first electrode and the second electrode to a preset value for generating a treatment-specific flux.

10. The method of claim 8, wherein the first electrode is a coil electrode and the second electrode is a coil electrode.

11. The method of claim 8, wherein the electro-osmosis is generated for a reduction up to a removal of the internal organ oedema.

12. The method of claim 8, wherein the current is a direct current.

13. The method of claim 12, wherein the direct current is an amplitude modulated direct current.

14. The method of claim 13, wherein the control unit is configured to switch the polarity of the direct current in predetermined time intervals.

15. The method of claim 14, wherein the predetermined time intervals comprise intervals between 10 minutes and three months.

16. The method of claim 8, wherein the control unit is configured to cause and maintain the strength of the electric current at the preset value independently of external influences.

17. A method for treating internal organ oedema, comprising
positioning a first electrode and a second electrode on or inside a subject such that that an electric current flow between the first and second electrodes traverses through the internal organ oedema of the subject; and
delivering a controlled electric current between the electrodes to the internal organ oedema, wherein the electrodes are connected to a control unit adapted to deliver the electric current to a preset value to induce electro-osmosis, wherein the preset value is maintained by controlling a voltage between the first electrode and the second electrode for any given distance between the electrodes,
wherein the first electrode is a patch electrode positioned on the epicardial side of the heart and wherein the second electrode is a coil electrode positioned inside the ventricular cavity of the heart.

18. The method of claim 17, wherein the control unit is adapted to charge the first electrode negatively and the second electrode positively, and the control unit is adapted to directly control a strength of the electric current induced by the first electrode and the second electrode to a preset value for generating a treatment-specific flux.

19. The method of claim 17, wherein the electro-osmosis is generated for a reduction up to a removal of the internal organ oedema.

20. The method of claim 17, wherein the current is a direct current.

21. The method of claim 20, wherein the direct current is an amplitude modulated direct current.

22. The method of claim 20, wherein the control unit is configured to switch the polarity of the direct current in predetermined time intervals.

23. The method of claim 22, wherein the predetermined time intervals comprise intervals between 10 minutes and three months.

24. The method of claim 22, wherein the predetermined time intervals comprise intervals between 24 hours and 7 days.

25. The method of claim 17, wherein the control unit is configured to cause and maintain the strength of the electric current at the preset value independently of external influences.

26. A method for treating internal organ oedema, comprising
positioning a first electrode and a second electrode on or inside a subject such that that an electric current flow between the first and second electrodes traverses through the internal organ oedema of the subject; and
delivering a controlled electric current between the electrodes to the internal organ oedema, wherein the electrodes are connected to a control unit adapted to deliver the electric current to a preset value to induce electro-osmosis, wherein the preset value is maintained by controlling a voltage between the first electrode and the second electrode for any given distance between the electrodes,
wherein the internal organ oedema is a myocardial oedema or an oedema of the kidney or an oedema of the liver.

27. The method of claim 26, wherein the control unit is adapted to charge the first electrode negatively and the second electrode positively, and the control unit is adapted to directly control a strength of the electric current induced by the first electrode and the second electrode to a preset value for generating a treatment-specific flux.

28. The method of claim 26, wherein the electro-osmosis is generated for a reduction up to a removal of the internal organ oedema.

29. The method of claim 26, wherein the current is a direct current.

30. The method of claim 29, wherein the direct current is an amplitude modulated direct current.

31. The method of claim 29, wherein the control unit is configured to switch the polarity of the direct current in predetermined time intervals.

32. The method of claim 31, wherein the predetermined time intervals comprise intervals between 10 minutes and three months.

33. The method of claim 31, wherein the predetermined time intervals comprise intervals between 24 hours and 7 days.

34. The method of claim 26, wherein the control unit is configured to cause and maintain the strength of the electric current at the preset value independently of external influences.

35. A method for treating internal organ oedema, comprising
positioning a first electrode and a second electrode on or inside a subject such that that an electric current flow between the first and second electrodes traverses through the internal organ oedema of the subject; and
delivering a controlled electric current between the electrodes to the internal organ oedema, wherein the electrodes are connected to a control unit adapted to deliver the electric current to a preset value to induce electro-osmosis, wherein the preset value is maintained by controlling a voltage between the first electrode and the second electrode for any given distance between the electrodes,
wherein the electro-osmosis generates an electroosmotic effect comprising an accumulation of oedema fluid at the electrodes to be carried away from the electrodes.

36. The method of claim 35, wherein the control unit is adapted to charge the first electrode negatively and the second electrode positively, and the control unit is adapted to directly control a strength of the electric current induced by the first electrode and the second electrode to a preset value for generating a treatment-specific flux.

37. The method of claim 35, wherein the electro-osmosis is generated for a reduction up to a removal of the internal organ oedema.

38. The method of claim 35, wherein the current is a direct current.

39. The method of claim 38, wherein the direct current is an amplitude modulated direct current.

40. The method of claim 38, wherein the control unit is configured to switch the polarity of the direct current in predetermined time intervals.

41. The method of claim 40, wherein the predetermined time intervals comprise intervals between 10 minutes and three months.

42. The method of claim 40, wherein the predetermined time intervals comprise intervals between 24 hours and 7 days.

43. The method of claim 35, wherein the control unit is configured to cause and maintain the strength of the electric current at the preset value independently of external influences.

44. A method for treating internal organ oedema, comprising
- positioning a first electrode and a second electrode on or inside a subject such that that an electric current flow between the first and second electrodes traverses through the internal organ oedema of the subject; and
- delivering a controlled electric current between the electrodes to the internal organ oedema, wherein the electrodes are connected to a control unit adapted to deliver the electric current to a preset value to induce electro-osmosis, wherein the preset value is maintained by controlling a voltage between the first electrode and the second electrode for any given distance between the electrodes,
- wherein the predetermined time intervals comprise intervals between 24 hours and 7 days.

* * * * *